(12) United States Patent
Bongberg et al.

(10) Patent No.: US 12,381,000 B1
(45) Date of Patent: Aug. 5, 2025

(54) DEFIBRILLATOR INCIDENT REPORTING AND DEFIBRILLATOR/EPCR INTEGRATION

(71) Applicant: Avive Solutions, Inc., San Francisco, CA (US)

(72) Inventors: Micah R. Bongberg, Kirkland, WA (US); Sameer Jafri, San Diego, CA (US); Rory M. Beyer, San Mateo, CA (US)

(73) Assignee: Avive Solutions, Inc., Brisbane, CA (US)

( * ) Notice: Subject to any disclaimer, the term of this patent is extended or adjusted under 35 U.S.C. 154(b) by 1021 days.

(21) Appl. No.: 17/217,738

(22) Filed: Mar. 30, 2021

Related U.S. Application Data

(60) Provisional application No. 63/004,320, filed on Apr. 2, 2020.

(51) Int. Cl.
*G16H 40/67* (2018.01)
*G06F 16/955* (2019.01)
*G16H 10/60* (2018.01)
*H04W 4/021* (2018.01)
*H04W 4/06* (2009.01)
*H04W 4/23* (2018.01)
*H04W 4/80* (2018.01)

(52) U.S. Cl.
CPC ......... *G16H 40/67* (2018.01); *G06F 16/9554* (2019.01); *G16H 10/60* (2018.01); *H04W 4/021* (2013.01); *H04W 4/06* (2013.01); *H04W 4/23* (2018.02); *H04W 4/80* (2018.02)

(58) Field of Classification Search
CPC ....... A61B 5/0006; A61B 5/332; A61B 5/053; A61B 5/316; A61B 5/33; A61B 5/346; A61B 5/4848; A61B 2505/01; A61B 5/282; A61B 5/335; A61B 5/339; A61B 5/361; A61B 5/363; A61B 5/742; A61B 50/30; A61B 5/7405
See application file for complete search history.

(56) References Cited

U.S. PATENT DOCUMENTS

| 6,292,687 | B1 | 9/2001 | Lowell et al. |
| 6,356,785 | B1 | 3/2002 | Snyder et al. |
| 6,493,581 | B2 | 12/2002 | Russell |
| 6,747,556 | B2 | 6/2004 | Medema et al. |

(Continued)

FOREIGN PATENT DOCUMENTS

| CN | 105013085 | 11/2015 |
| CN | 108671401 | 10/2018 |

(Continued)

OTHER PUBLICATIONS

Eftestøl T, Sherman LD. "Towards the automated analysis and database development of defibrillator data from cardiac arrest." Biomed Research International; Epub Jan. 12, 2014.; 19 pages (Year: 2014).*

(Continued)

*Primary Examiner* — Rachel L. Porter
(74) *Attorney, Agent, or Firm* — Beyer Law Group LLP (57) ABSTRACT

A variety of methods, defibrillators, defibrillator network servers and system architectures are described that facilitate conveying defibrillator incident information to personnel that can benefit from access to such defibrillator incident information.

20 Claims, 4 Drawing Sheets

(56) References Cited

U.S. PATENT DOCUMENTS

| | | | |
|---|---|---|---|
| 6,834,207 | B2 | 12/2004 | Miyauchi et al. |
| 6,937,150 | B2 | 8/2005 | Medema et al. |
| 7,289,029 | B2 | 10/2007 | Medema et al. |
| 8,086,320 | B2 | 12/2011 | Saketkhou |
| 8,180,457 | B2 | 5/2012 | Matos |
| 8,209,008 | B2 | 6/2012 | Hansen et al. |
| 8,565,871 | B2 | 10/2013 | Tuysserkani |
| 8,706,225 | B2 | 4/2014 | Matos |
| 8,818,522 | B2 | 8/2014 | Mass et al. |
| 8,880,168 | B2 | 11/2014 | Pearce et al. |
| 8,981,927 | B2 | 3/2015 | McSheffrey |
| 9,026,147 | B2 | 5/2015 | Galvin et al. |
| 9,035,787 | B2 | 5/2015 | Bongberg et al. |
| 9,101,527 | B2 | 8/2015 | Madanat |
| 9,232,040 | B2 | 1/2016 | Barash et al. |
| 9,289,621 | B2 | 3/2016 | Aoyama et al. |
| 9,295,849 | B2 | 3/2016 | Elghazzawi et al. |
| 9,307,383 | B1 | 4/2016 | Patrick |
| 9,324,120 | B2 | 4/2016 | Braun |
| 9,480,852 | B2 | 11/2016 | Bonnamy |
| 9,498,152 | B2 | 11/2016 | Bowers |
| 9,592,401 | B2 | 3/2017 | Freeman et al. |
| 9,619,767 | B2 | 4/2017 | Braun |
| 9,628,946 | B2 | 4/2017 | Elghazzawi |
| 9,847,030 | B2 | 12/2017 | Kadobayashi et al. |
| 9,848,058 | B2 | 12/2017 | Johnson et al. |
| 9,872,998 | B2 | 1/2018 | Aoyama et al. |
| 9,889,311 | B2 | 2/2018 | Horseman et al. |
| 9,897,459 | B2 | 2/2018 | Johnson |
| 9,987,193 | B2 | 5/2018 | Freeman |
| 10,035,023 | B2 | 7/2018 | Das |
| 10,058,469 | B2 | 8/2018 | Freeman |
| 10,058,709 | B2 | 8/2018 | Tilton, Jr. |
| 10,090,716 | B2 | 10/2018 | Stever et al. |
| 10,092,767 | B1 | 10/2018 | Newton et al. |
| 10,099,061 | B2 | 10/2018 | Buchanan |
| 10,159,848 | B2 | 12/2018 | Amann et al. |
| 10,178,534 | B2 | 1/2019 | Barash et al. |
| 10,298,072 | B2 | 5/2019 | Stever et al. |
| 10,381,118 | B2 | 8/2019 | Kellum |
| 10,449,380 | B2 | 10/2019 | Andrews |
| 10,504,622 | B2 | 12/2019 | Gallopyn et al. |
| 10,543,379 | B2 | 1/2020 | Hingston et al. |
| 10,565,845 | B1 | 2/2020 | Beyer et al. |
| 10,580,280 | B1 | 3/2020 | Picco et al. |
| 10,621,846 | B1 | 4/2020 | Beyer et al. |
| 10,638,929 | B2 | 5/2020 | Kaib et al. |
| 10,657,796 | B2 | 5/2020 | Bowers |
| 10,665,078 | B1 | 5/2020 | Picco et al. |
| 10,744,063 | B2 | 8/2020 | Freeman |
| 10,792,506 | B2 | 10/2020 | Elghazzawi |
| 10,796,396 | B2 | 10/2020 | Braun et al. |
| 10,806,939 | B1 | 10/2020 | Malott et al. |
| 10,857,371 | B2 | 12/2020 | Gustavson et al. |
| 10,861,310 | B2 | 12/2020 | Picco et al. |
| 10,946,209 | B2 | 3/2021 | Andrews et al. |
| 10,957,178 | B2 | 3/2021 | Beyer et al. |
| 12,144,584 | B2 | 11/2024 | Freeman et al. |
| 2003/0149759 | A1 | 8/2003 | Hetherington et al. |
| 2004/0015191 | A1 | 1/2004 | Otman et al. |
| 2004/0049233 | A1 | 3/2004 | Edwards |
| 2004/0064342 | A1 | 4/2004 | Browne et al. |
| 2006/0030891 | A1 | 2/2006 | Saltzstein et al. |
| 2006/0041278 | A1 | 2/2006 | Cohen et al. |
| 2006/0149321 | A1 | 7/2006 | Merry et al. |
| 2006/0149322 | A1 | 7/2006 | Merry et al. |
| 2006/0149323 | A1 | 7/2006 | Merry et al. |
| 2007/0032830 | A1 | 2/2007 | Bowers |
| 2007/0136099 | A1 | 6/2007 | Neligh et al. |
| 2007/0162075 | A1 | 7/2007 | O'hara |
| 2007/0270909 | A1 | 11/2007 | Saketkhou |
| 2007/0299473 | A1 | 12/2007 | Matos |
| 2008/0250166 | A1 | 10/2008 | Edwards |
| 2009/0070148 | A1 | 3/2009 | Skocic |
| 2009/0149894 | A1 | 6/2009 | Merry et al. |
| 2009/0284378 | A1 | 11/2009 | Ferren et al. |
| 2010/0017471 | A1 | 1/2010 | Brown et al. |
| 2010/0286490 | A1 | 11/2010 | Koverzin |
| 2011/0060378 | A1 | 3/2011 | Tuysserkani |
| 2011/0071880 | A1 | 3/2011 | Spector |
| 2011/0117878 | A1 | 5/2011 | Barash et al. |
| 2011/0152702 | A1 | 6/2011 | Goto |
| 2012/0232355 | A1 | 9/2012 | Freeman |
| 2013/0012151 | A1 | 1/2013 | Hankins |
| 2013/0065628 | A1 | 3/2013 | Pfeffer |
| 2013/0087609 | A1 | 4/2013 | Nichol et al. |
| 2013/0296719 | A1 | 11/2013 | Packer et al. |
| 2014/0002241 | A1 | 1/2014 | Elghazzawi |
| 2014/0004814 | A1 | 1/2014 | Elghazzawi |
| 2014/0031884 | A1 | 1/2014 | Elghazzawi |
| 2014/0222096 | A1 | 8/2014 | Hu et al. |
| 2014/0222466 | A1 | 8/2014 | Kellum |
| 2014/0266718 | A1 | 9/2014 | Bongberg et al. |
| 2015/0178457 | A1* | 6/2015 | Grimley ............... G06F 3/04817 |
| | | | 705/3 |
| 2015/0206408 | A1 | 7/2015 | LaLonde et al. |
| 2015/0343229 | A1 | 12/2015 | Peterson et al. |
| 2016/0066653 | A1 | 3/2016 | Piva et al. |
| 2016/0133160 | A1 | 5/2016 | Packer et al. |
| 2016/0140834 | A1 | 5/2016 | Tran |
| 2016/0148495 | A1 | 5/2016 | Buchanan |
| 2016/0210581 | A1 | 7/2016 | Braun |
| 2016/0213942 | A1 | 7/2016 | Elghazzawi et al. |
| 2016/0328950 | A1 | 11/2016 | Pelletier et al. |
| 2017/0028211 | A1 | 2/2017 | Tilton, Jr. |
| 2017/0172424 | A1 | 6/2017 | Eggers et al. |
| 2017/0251347 | A1 | 8/2017 | Mehta et al. |
| 2017/0281016 | A1 | 10/2017 | Elghazzawi |
| 2017/0281461 | A1 | 10/2017 | Kokubo et al. |
| 2017/0289350 | A1 | 10/2017 | Philbin |
| 2017/0325091 | A1* | 11/2017 | Freeman ................ H04W 4/90 |
| 2017/0367927 | A1 | 12/2017 | Cervantes |
| 2018/0169426 | A1 | 6/2018 | Montague et al. |
| 2018/0369598 | A1 | 12/2018 | Newton et al. |
| 2019/0038133 | A1 | 2/2019 | Tran |
| 2019/0044362 | A1 | 2/2019 | Beyer et al. |
| 2019/0099608 | A1 | 4/2019 | Elghazzawi et al. |
| 2019/0117983 | A1 | 4/2019 | Andrews et al. |
| 2019/0117984 | A1 | 4/2019 | Andrews et al. |
| 2019/0117987 | A1 | 4/2019 | Beyer et al. |
| 2019/0117988 | A1 | 4/2019 | Beyer et al. |
| 2019/0159009 | A1* | 5/2019 | Barash ................ G08B 25/005 |
| 2019/0168010 | A1 | 6/2019 | Elghazzawi |
| 2019/0174289 | A1 | 6/2019 | Martin et al. |
| 2019/0279327 | A1 | 9/2019 | Braun et al. |
| 2019/0306664 | A1 | 10/2019 | Mehta et al. |
| 2019/0318827 | A1 | 10/2019 | Chiu et al. |
| 2019/0381330 | A1* | 12/2019 | Aoyama ............... A61N 1/3968 |
| 2020/0054885 | A1 | 2/2020 | Aprile |
| 2020/0090483 | A1 | 3/2020 | Picco et al. |
| 2020/0092700 | A1 | 3/2020 | Picco et al. |
| 2020/0206517 | A1 | 7/2020 | Martin et al. |
| 2020/0221263 | A1 | 7/2020 | Sturman et al. |
| 2020/0242907 | A1 | 7/2020 | Beyer et al. |
| 2020/0286352 | A1 | 9/2020 | Beyer et al. |
| 2020/0286353 | A1 | 9/2020 | Jafri et al. |
| 2020/0373005 | A1 | 11/2020 | Halsne et al. |
| 2022/0157418 | A1* | 5/2022 | Ashmore ............... G16H 15/00 |

FOREIGN PATENT DOCUMENTS

| | | |
|---|---|---|
| CN | 111539866 | 8/2020 |
| DE | 202004002106 | 6/2004 |
| EP | 1157717 | 1/2005 |
| EP | 2218478 | 8/2010 |
| EP | 2879759 | 10/2019 |
| JP | 2001/325689 | 11/2001 |
| KR | 20160012239 | 2/2016 |
| KR | 101780214 | 10/2017 |
| KR | 102152282 | 9/2020 |

(56) References Cited

FOREIGN PATENT DOCUMENTS

| WO | 2010/66014 | 6/2010 |
|----|------------|--------|
| WO | 2018/069383 | 4/2018 |

OTHER PUBLICATIONS

Beyer et al., U.S. Appl. No. 17/100,154, filed Nov. 19, 2020.
Bongberg et al., U.S. Appl. No. 17/100,313, filed Nov. 19, 2020.
Bongberg et al., U.S. Appl. No. 17/217,738, filed Mar. 30, 2021.

* cited by examiner

DEFIBRILLATOR INCIDENT REPORTING AND DEFIBRILLATOR/EPCR INTEGRATION

CROSS-REFERENCE TO RELATED APPLICATIONS

The present application claims the priority of U.S. Provisional Patent Application No. 63/004,320, filed on Apr. 2, 2020, which is incorporated herein by reference in its entirety.

FIELD

The present disclosure relates to methods, devices and systems for getting automated external defibrillators (AEDs) incident data into an electronic patient's record associated with a patient treated using the AED.

BACKGROUND

Sudden cardiac arrest is one of the leading causes of death. In the United States alone, roughly 350,000 people die each year from sudden cardiac arrest. It is the leading cause of death for individuals over 40 and the #1 killer of student athletes. The most effective treatment for sudden cardiac arrest is the use of CPR coupled with defibrillation. Automated external defibrillators (AEDs) are portable devices designed to automatically check for life-threatening heart rhythms associated with sudden cardiac arrest and to send an electrical shock to the heart to try to restore a normal rhythm when shockable heart rhythms are detected. The two most common conditions treated by AEDs are Pulseless Ventricular tachycardia (aka VT or V-Tach) and Ventricular fibrillation (VF or V-Fib). AEDs are typically designed so that they can be used by a lay person in situations where professional medical help is not available.

When an AED is used to treat a potential cardiac arrest, it will typically collect or create information about the incident that may be useful to doctors and other medical personnel that later treat the patient. Although such information can be quite helpful to medical personnel, many AEDs don't have an easy-to-use mechanism for gathering and/or delivering such information to appropriate medical personnel. Some AEDs create an incident report that can be loaded onto an insertable/removable memory stick or memory card. Responding emergency services personnel (e.g. EMTs) can then deliver the memory device to medical personnel or manually transfer the incident report from the memory stick or memory card into a patient related record. In some other approaches, the AED is able to convey incident information to responding EMS personnel. Although existing approaches can be useful, there are continuing efforts to provide improved mechanisms that can simply and reliably get AED incident information into the victim' patient medical records and/or make such incident information available to medical personnel.

SUMMARY

To achieve the foregoing and other objects, a variety of methods, defibrillators, defibrillator network servers and system architectures are described that facilitate conveying defibrillator incident information to personnel that can benefit from access to such defibrillator incident information.

In one aspect, an AED outputs or displays an incident identifier at the scene of an emergency use of the AED to treat a victim of a potential cardiac arrest. In some embodiments, this facilitates entry of the incident identifier into an emergency services electronic patient care record associated with the incident. Separately, the AED creates an incident log and transmits the incident log directly or indirectly to a remotely located management server. Preferably, the incident log includes at least one of the incident identifier, and elements that can be used to generate the incident identifier. The management server is configured to create an incident report based at least in part of the incident log. When the management server, receives a request from an Electronic Patient Care Record (ePCR) system for a defibrillator incident report, it transmits the incident report to the ePCR system for inclusion in the electronic patient care record associated with the incident.

In some circumstances, the incident identifier is displayed to facilitate an emergency responder at the scene of the potential cardiac arrest incident manually entering the incident identifier into the electronic patient care record associated with the incident.

In some embodiments, the incident identifier is displayed on at least one selected from the group consisting of: a display screen on the AED; a display screen on an interface unit attached to or associated with the AED; and a display screen of a mobile communication device at the scene of the incident that received the incident identifier from the AED.

In some embodiments, the incident identifier is wirelessly transmitted (e.g. broadcast as a BLE advertisement) by the AED and received by an ePCR input device at the scene of the incident and is automatically or semi-automatically entered into the electronic patient care record. Alternatively or additionally, the incident identifier may be displayed on a device used by the emergency services personnel (e.g., on a Smartphone or a tablet computer) to facilitate entry into the patient care record.

In some embodiments, the incident report request received from the ePCR system further includes at least one of a geo-location of the incident and a time of the incident. When such information is available, the management server may utilize the at least one of the geo-location of the incident and the time of the incident in conjunction with the incident identifier to help ensure, authenticate or verify that the correct incident report is transmitted to the ePCR system in response to the incident report request. In some alternate embodiments, the geo-location of the incident and the time of the incident may be used in place of the incident identifier to identify the appropriate incident report.

In some embodiments, the incident identifier is embedded in a displayed barcode. The barcode can be a two dimensional barcode such as a QR code or any other suitable barcode. In various embodiments, the displayed barcode is a QR code that is created by one of the AED, an interface unit or a mobile communication device. When a barcode is used, the emergency responder can scan the barcode to enter the incident identifier into the ePCR system. Similarly, the barcode may be scanned by other bystanders to obtain the incident identifier.

In some embodiments, the emergency responder transfers the incident report to a medical facility record system together with the electronic patient care record associated with the incident.

In some embodiments, the incident report transmitted to the ePCR system is in the form of a PDF file.

In another aspect an automated external defibrillator (AED) system is configured to create an incident log or status message associated with an emergency use of the AED system. The incident log or status message includes an incident identifier. The AED system also displays a barcode that includes the incident identifier. The AED system further transmit the incident log or status message directly or indirectly to an AED network server, which can create an incident report based at least in part on the incident log or status message.

In some embodiments, the barcode further includes a URL of a website from which the incident report based can be viewed and/or downloaded.

In various embodiments, the barcode may be created and/or displayed by at least one selected from the group consisting of: a display screen on the AED; a display screen on an interface unit attached to or associated with the AED; and a display screen of a mobile communication device at the scene of the incident that received the incident identifier from the AED.

In another method aspect, a barcode that includes both a defibrillator incident identifier and a URL is scanned. In some embodiments, the scanning may be done at the scene of an emergency use of the defibrillator corresponding to the incident. A defibrillator incident report is thereafter accessed from a website associated with the URL referenced by the barcode. The incident identifier is used at least in part to identify the defibrillator incident report corresponding to the incident.

In still another aspect, other methods of communicating defibrillator incident information created by an automated external defibrillator (AED) during emergency use of the AED are described. In some embodiments, the AED, locally outputs or displays an incident identifier that identifies the incident. The AED also creates an incident log that provides incident information based on the emergency use of the AED. The incident log is transmitted directly or indirectly from the AED to a remotely located AED management server and includes at least one of the incident identifier, and elements that can be used to generate the incident identifier. The AED management server, generates an incident report associated with the incident, based at least in part on the incident report. When the AED management server receives a request for the incident report from a requester that includes the incident identifier, it transmits the incident corresponding incident report to the requester.

In some embodiments, the request for the incident report is received from a medical records system. In such circumstances, the incident report is sent to the medical records system it is entered into a patient record associated with the victim.

In some embodiments, the incident identifier is output by the AED as part of a status message wirelessly broadcast by the AED as an advertisement without requiring the establishment of a wireless connection between the AED and a listener that receives the status message.

In some embodiments, the incident identifier is displayed at a scene of the incident and is recorded or captured in a manner that facilitates use of the recorded or captured incident identifier in the request for the incident report. As previously mentioned, in some embodiments, the incident identifier may be rendered as part of a QR code or other barcode.

BRIEF DESCRIPTION OF THE DRAWINGS

The invention and the advantages thereof, may best be understood by reference to the following description taken in conjunction with the accompanying drawings in which.

In the drawings, like reference numerals are sometimes used to designate like structural elements. It should also be appreciated that the depictions in the figures are diagrammatic and not to scale.

DETAILED DESCRIPTION

Emergency medical services (EMS) such as ambulance and paramedic services and/or emergency services personnel operating in other out of hospital or pre-hospital environments provide urgent pre-hospital treatment and stabilization for serious illness and injuries and often facilitate transport to definitive care locations. The emergency services personnel that provide such services include emergency services technicians (EMTs), paramedics and others and are collectively referred to as EMS personnel herein. Most modern EMS providers have electronic records systems that they utilize to input medical information relating to the out-of-hospital medical incidents that they respond to. When a patient is transported to a hospital, the record created by the EMS personnel is electronically transferred to the hospital so that it can be entered appropriately into the patient's medical records.

The electronic patient records created by the EMS personnel are sometimes referred to as ePCR records. There are a number of interpretations of what ePCR stands for, as for example, "Electronic Patient Care Records", "Emergency Patient Care Records", "Electronic Pre-hospital Care Reports", etc. Other vendors refer to such products as Electronic Health Reports (EHR) or utilize other suitable terms. As used herein, the term ePCR is intended to refer to the types of electronic patient records created by EMS personnel to document out-of-hospital medical incidents that such personnel respond to. This is distinguished from the electronic medical records (eMRs) that are maintained by medical institutions such as hospitals and doctor offices-which, somewhat confusingly, are also sometimes referred to as patient care records (PCR). There are continuing efforts to provide more integration and consolidation between these two types of systems (i.e., between ePCR and eMR systems but at least presently, they tend to be separate systems.

When a patient/victim experiences cardiac arrest outside of a hospital or other dedicated medical facility setting, EMS is typically called to respond to the incident. When an AED has been deployed prior to the arrival of EMS personnel, the AED may have information that may be helpful to medical personnel that later treat the victim. Thus, as outlined in the background, it is desirable to provide mechanisms for getting incident information from the treating AED into the patient's medical records (eMR).

Figure 1:
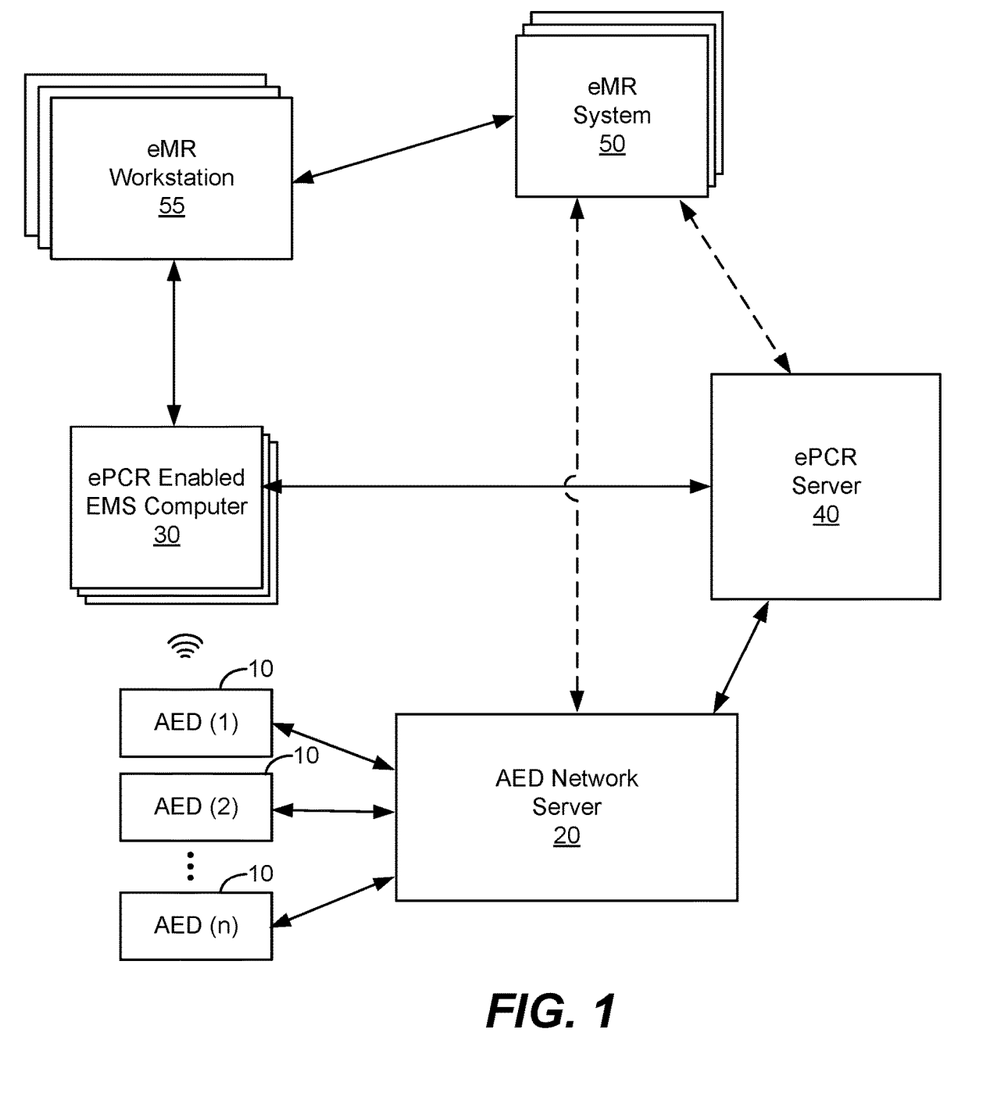
FIG. 1 is a block diagram of a network having components suitable for implementing an AED Incident Reporting flow in accordance with a first embodiment.

FIG. 1 illustrates selected components of a system that is architected to deliver defibrillator incident information from a defibrillator (e.g., an AED) to a medical records system that is accessible to medical personnel that may treat or otherwise care for a victim of cardiac arrest—as for example, a medical records system associated with a care facility (e.g., a hospital, doctors office or other suitable medical facility). The illustrated embodiment includes a multiplicity of AEDs 10, an AED network server 20, ePCR enabled EMS computers 30 carried by EMS personnel (e.g. first responders); one or more ePCR systems 40; one or more electronic medical records systems (50) as associated workstations (55) that can interface with the medical records system 50. In some embodiments, the incident information is presented to the medical records system in the form of an AED incident report.

In the described system, connected AEDs 10 are configured to generate an incident report or incident log file (collectively referred to as an incident log herein) each time it is activated and used in an emergency setting. The specific contents of the incident log may vary widely in accordance with the design goal of any particular system, however, representative incident information may include information such as:

1) A unique incident identifier (Incident ID). The Incident ID can be assigned in any manner desired, so long as it is uniquely identifies the incident log sufficiently so that reports from two different AEDs or for two different uses of an AED don't inadvertently create the same Incident ID which could lead to the transmission of the wrong report. In some implementations, the Incident ID may be a UID such as a concatenation or hash of the AED's serial number and activation time. In other implementations, a simpler Incident ID may be used.
2) The time the AED was activated.
3) The number of shocks delivered by the AED and the respective timing of each. In some applications, the shock timing may be reported in terms of time from AED activation rather than calendar time.
4) The results and timing of each heart rhythm classification analysis made by the AED. In some instances this might be simple determination such as whether the detected cardiac rhythm is shockable or not-shockable and the time the analysis was made. In other instances, when the AED has the capability of identifying the nature of the rhythm more specifically (e.g., pulseless ventricular tachycardia, ventricular fibrillation, etc.), the more detailed classification may be provided.
5) The energy delivered in each shock (e.g. 50 joules, 150 joules, 200 joules, etc.) and the nature of the shock waveform delivered (e.g., bi-phasic exponential, etc.)
6) When recordings of the detected heart rhythms are available, some or all of the detected ECG may also be included (e.g., the entire ECG recorded by the AED during its activation, each ECG segment detected by the AED, selected ECG segments/snippets such as the ECG segments/snippets used in each shock decision and/or ECG segments/snippets detected slightly after any shock is delivered, etc.).
7) A geo-location of the incident—e.g. the geographic coordinates of the incident as provided by a GNSS (e.g., GPS) system.
8) Other patient information collected by the AED and/or associated equipment—which could include environmental readings, oximeter readings, detected patient impendence, impedance graphs, etc.
9) Detected information about CPR performed during the incident—e.g., frequency and/or depth of compressions, etc.
10) Information about the use of the AED itself—e.g., a serial number of the AED itself, a serial number or type of the pads used by the AED during the incident, an operating mode that the AED was used in (e.g., adult or pediatric mode), a language that instructions were given in, timestamps of various audio instructions or events that take place over the course of the incident, etc.
11) Timestamps of events that occurred during the incident and/or time associated with various steps in the treatment sequence. For example the time taken from power-on to electrode pad removal; the time that it take from pad removal to pads applied (i.e., when a patient is detected), etc.

Of course, any other appropriate information that is available to the AED may be included in the incident log as well. In some implementations, the incident log/report is made available after the AED is no longer being used to monitor or deliver treatment to the patient. However, in other implementations, the incident log/report may be created and made available during the emergency use of the AED. In still others, it may be a hybrid, where some information is available in real-time during the incident and other information is not available until conclusion of the incident.

The AEDs 10 preferably have features that facilitate communicating information. Such features may include a display screen, wireless communications ability (e.g., Bluetooth, cellular, Wi-Fi, etc.), and/or other components. In some instances such features and/or capabilities may be integrated into the AED itself. In others, such features and/or capabilities may be provided in whole or in part by an interface unit (or multiple interface units) that is/are separate from, but used in connection with the AED. By way of example, Applicant has developed AED interface units incorporating a display and communication abilities that is adapted to be mounted on and detachably attached to an AED. With this arrangement, the AED and interface unit may be carried together as a unitary portable unit. By way of example, some representative interface units are described in U.S. Pat. Nos. 10,737,105 and 10,773,091, each of which is incorporated herein by reference. Of course, other existing and proposed AEDs have incorporated or proposed various levels of communication capabilities or are configured to work with separate communication units that facilitate communications with remote servers.

In other circumstances, the interface unit may be incorporated into a dock or cabinet that holds the AED or in other separate devices. In still other embodiments, some or all of the interface functionalities may be provided by an external device (e.g. a Smartphone or other mobile communication device) having an app or other software installed thereon that is suitable for providing the desired interface functionalities. For example, Applicant is also developing an AED that is capable of communicating with remote devices via other intermediaries, such as a bystander's mobile communications device (e.g. cellular Smartphones) and/or other suitable configured nearby devices. By way of example, some such AEDs are described in U.S. patent application Ser. No. 16/733,591 (now U.S. Pat. No. 11,452,881) and PCT Application No. PCT/US20/12146, which are also each incorporated by reference.

The AED network server 20 may take a variety of forms. Often, it may be an AED management server that coordinates management of the AEDs. In other circumstances, the AED network server 20 may be part of an AED responder network server which can be used to notify AEDs and/or volunteer responders of nearby cardiac arrest incidents and/or to facilitate communications between a Public Safety Answering Point (PSAP) and an AED during emergency use of the AED. A few such network servers are described in U.S. Pat. Nos. 10,580,280 and 10,621,846 and U.S. patent application Ser. Nos. 17/100,154 and 17/155,852 (now U.S. Pat. No. 11,210,919), each of which are incorporated herein by reference. In still other circumstances it may be a network server dedicated entirely or in part to coordinating communication of defibrillator incident reports. Of course the AED network server 20 may perform any combination of these function and/or other functions as may be appropriate for any given implementation.

EMS computers 30 are provided by a variety of vendors and are commonly carried and used by emergency services personnel when responding to emergency calls. There are a number of ePCR providers and EMS computers commonly include ePCR software applications that facilitate the creation of electronic patient care records for victims treated by the EMS personnel. The ePCR system 50 typically includes back-end server(s) that coordinate a variety of services provided by the ePCR system.

Most modern medical providers have some sort of electronic medical records system 50. Again, there are a number of existing vendors that provide such system.

Figure 2:
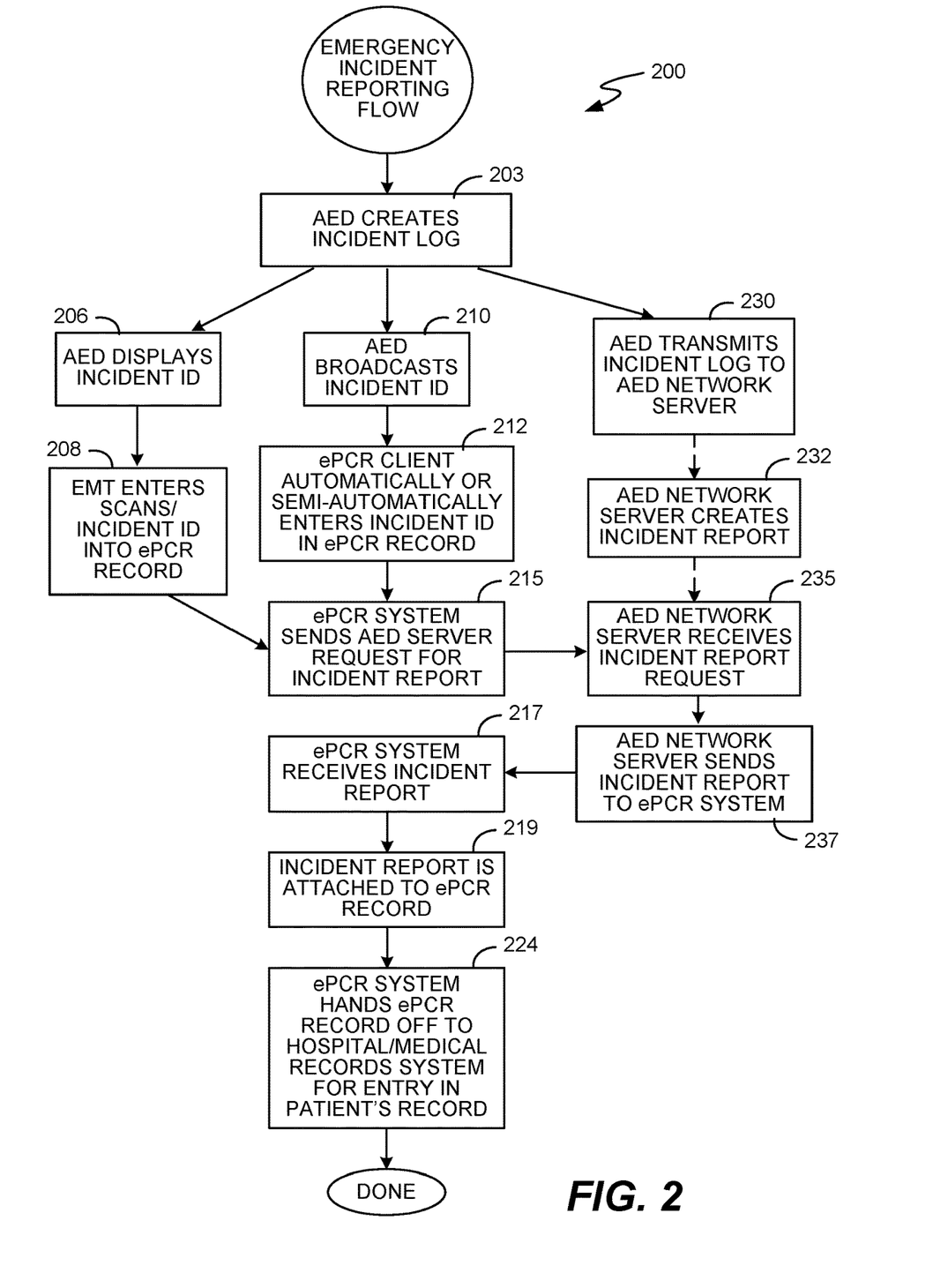
FIG. 2 is a flow chart illustrating an AED Incident Reporting flow in accordance with the first embodiment.

Referring next to FIG. 2, a defibrillator incident reporting flow in accordance with a first embodiment will be described that leverages the existing ePCR infrastructure and standard EMS processes to facilitate delivering defibrillator incident reports into a medical provider's electronic medical records (eMR) system.

Figure 3:
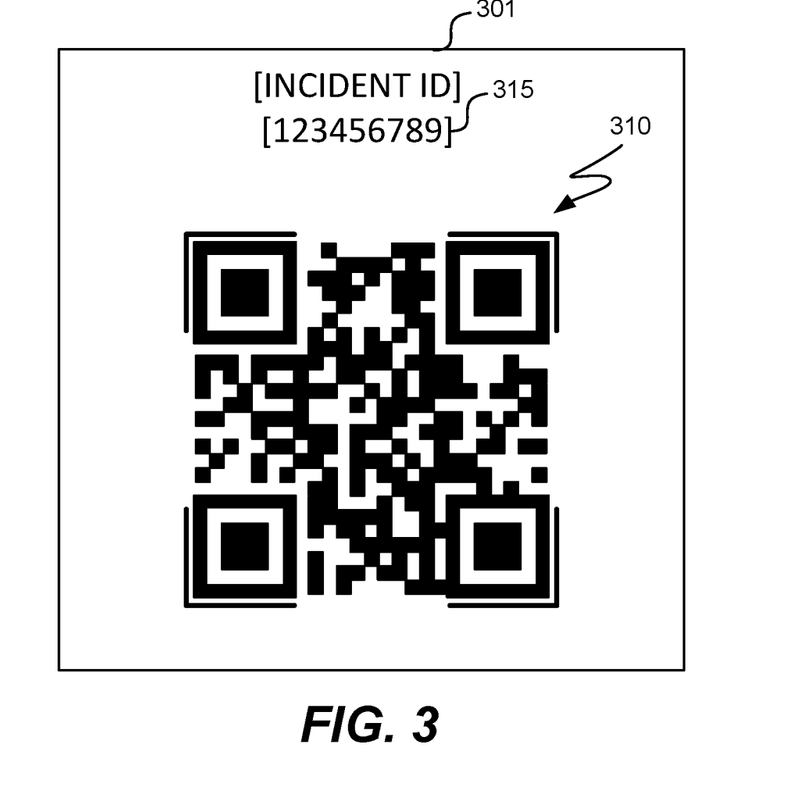
FIG. 3 is a screen shot illustrating the display of an Incident ID in the form of both a QR code and an alphanumeric identifier.

After the AED has been used and/or during its use, the AED makes the Incident ID available to the AED's user, bystanders and/or EMS personnel. In some embodiments, this is accomplished (at least in part) by displaying the Incident ID on the AED's display screen, or the display screen of an interface unit or other device that is associated with the AED as represented by block 206. A responding EMT can then enter the Incident ID into the patient's record in an Electronic Patient Care Reporting (ePCR) system as represented by block 208. As will be appreciated by those familiar with modern emergency medical services, most EMS personnel have access to an ePCR system. Most typically their ePCR system has a client application that is loaded on an emergency response computer—e.g., a laptop or tablet computer that is carried in the ambulance or other emergency response vehicle. The Incident ID may be entered in a variety of manners. In some circumstances or implementations, the responding EMT may manually enter the displayed Incident ID into the ePCR patient record. In other circumstances, the displayed Incident ID may take the form of, or include, a barcode that can be scanned by the EMT and thereby electronically entered into the ePCR record. Any type of barcode or analogous product code can be used for such purposes, including lineal barcodes, 2D barcodes, Universal Product Codes (UPC), International Article Number (EAN) codes, matrix codes, Quick Response (QR) codes, etc. By way of example, illustrates a 2D barcode, specifically a QR code 310, that is well suited for such purposes. Many electronic devices including some emergency response computers 30 incorporate barcode/QR code readers. As such, the ePCR client for emergency response computers having an installed barcode/QR reader can readily be configured to enter the Incident ID from the scanned code into the patient record. In some embodiments, the scanned code may also provide the IP address of a website from which an Incident Report may be viewed or downloaded.

It should be appreciated that the Incident ID may be conveyed to the EMTs in a variety of other ways in parallel with, or in place of, displaying the Incident ID on the AED's display screen. For example, the Incident ID may alternatively or additionally be broadcast by the AED's speaker. Audio broadcasts of the Incident ID can be particularly helpful when the AED doesn't have a display screen.

The Applicant is developing AEDs that are capable of broadcasting BLE advertisements as described, for example, in U.S. patent application Ser. Nos. 16/733,591 and 16/733,684 (now U.S. Pat. Nos. 11,452,881 and 11,077,312) which are incorporated herein by reference. In some implementations, the AED may include the Incident ID as part of status messages that the AED regularly broadcasts during and after emergency use of the AED. Such broadcasts are represented by block 210. When the EMT has a suitably configured listener, the listener receives the status message and can handle it appropriately. When the EMT computer that contains the ePCR client application contains a listener, the Incident ID can be automatically entered directly into the patient's record in the ePCR system. (Block 212). In fully automatic implementations, the Incident ID may be entered in the current patient record without requiring actions by the EMT. In semi-automatic implementations, the EMT may be prompted that an AED Incident ID is available, but must take some action to cause the Incident ID to be entered into the patient record. Such actions may be simple and intuitive such as selecting a GUI button or other GUI widget to authorize the entry of the Incident ID into the patient record. In other implementations, higher levels of authentication may be required.

In implementations where the listener is a device other than the emergency response computer (e.g., a mobile phone or other mobile communication device), the listener device may display the Incident ID so that it may be entered into the ePCR system manually by the EMT as previously described. Similar approaches can be used when the EMT computer functions as a listener but is not configured to automatically update the patient record.

The communication abilities of the AED enable the AED to transmit information directly or indirectly to AED network server 20. Accordingly, the AED is further configured to transmit the Incident ID and the incident log to the AED network server. (Block 230). Therefore, the incident log is generally available at the AED network server. The incident log may be transmitted directly by the AED itself, or indirectly via an interface device or other suitably configured device. Representative mechanisms for transmitting the incident log to the AED network server are described in the incorporated '591 and '684 applications, as well as U.S. Pat. No. 10,773,091 which is also incorporated herein by reference. Typically the Incident ID will be a part of the incident log, although that is not technically required since the AED network server can associate the Incident ID with the incident log as necessary. Preferably the geo-coordinates (e.g., the GPS coordinates) of the incident are also transmitted to the AED network server. Again, the GPS coordinates may be included in the incident log or transmitted separately.

In some embodiments, the AED network server 20 is configured to generate an Incident Report based on the incident log as represented by block 232. The Incident Report may include the full incident log file or it may be created based on the incident log file. In some implementations the Incident Report is provided in a standardized format that is easily read and printed such as a PDF so that the medical record system that eventually receives the receiving system doesn't need to have any special understanding of the format of the incident log or report. In other embodiments, the Incident Report may be generated by the AED itself and transmitted to the AED network server 20 in a format suitable for forwarding to medical record systems.

Once the ePCR system has the Incident ID, the Incident Report can readily be retrieved from the AED Network Server by sending an authenticated request for the Incident Report to the AED Network Server (step 215). When the AED network server receives an Incident Report Request (step 235) it retrieves (or generates) the Incident Report that corresponds to the received Incident ID and sends the Incident Report to the requesting ePCR (step 237). The ePCR system can then attach the defibrillator's Incident Report to the patient's ePCR record (step 219).

The EMT can manually initiate the Incident Report Request at any time. This can be at the scene of the incident, in transit to a hospital or urgent care center, after transferring the patient to the hospital or at any other suitable time. In other systems, the Incident Report Request can be generated automatically—as for example, in response to the detection of a defibrillator Incident ID in a field in an Incident ID field in the patient's record.

Conventionally, the ePCR record is transferred to the appropriate hospital/medical record system in connection with the transfer of a patient to a hospital, urgent care center or other suitable medical facility. The ePCR record is then entered in the patient's medical record. As long as the Incident Report has been attached to the ePCR record before the ePCR record is transferred, it is automatically transferred to hospital/medical records system together with the rest of the ePCR record. In this manner, the Incident Report can simply and reliably be included in the patient's medical records. Some medical centers still use paper records, and if that is the case, the ePCR record is typically printed and placed in the patient's file. In such circumstances, the Incident Report is printed and placed in the patient file together with the remainder of the ePCR report.

The workflow described above has several advantages and leverages processes that are already followed by many EMS providers. As will be appreciated by those familiar with emergency services operations, EMS are called in a very high percentage of the circumstances in which an AED is used in response to an out-of-hospital cardiac arrest incident. As such, the described workflow is appropriate for a high percentage of AED use cases. Furthermore, relatively simple and straight forward integrations between the AED network provider and the ePCR system providers is all that is necessary to facilitate delivering Incident Reports for any AED in the AED provider's network into the records of a wide variety of different medical providers. As will be apparent to those familiar with the field, there are a relatively limited number of commercially available ePCR systems, and there are a relatively limited number of AED manufacturers. As such, each such integration has the potential to facilitate Incident Report delivery in a large number of AED use cases.

The described system also does not require any special/different EMS hardware. Rather, relatively simple and straight forward software upgrades are all that are required to implement manual input implementations. At the same time, for any EMS hardware that already has listener capabilities (e.g., is BLE enabled), the system can be readily enhanced to facilitate automated or semi-automated Incident ID capture. By limiting the EMS personnel's required actions to simple and straight-forward tasks, the process does not unduly burden the EMS personnel and training is very simple. Furthermore, standard practices already involve uploading the EMS patient's ePCR record to the receiving medical facilities patient records system, so when the defibrillator Incident Report is retrieved prior to uploading no (or virtually no) extra work is required at that point of transferring the Incident Report to the medical facility.

The described workflow also has some security advantages because requests from defibrillator Incident Report from ePCR systems are from known and trusted systems that can be white-listed or otherwise handled as trusted requests.

For convenience, the Incident Report is often transmitted to the ePCR system in a format that can readily be attached to the ePCR record (e.g., as a PDF document). However, if/when desired by the ePCR provider, it should be appreciated that the incident information can be provided in any form desired by the ePCR provider, including as an incident log file, so that the ePCR system can generate its own Incident Report from (or that includes) the incident information provided.

The discussion above focuses on Incident Report Requests made in an effort to integrate the Incident Report into a patient record. However, it should be appreciated that EMS or medical personnel (or any other authorized user) may view and/or otherwise access the Incident Report in the same manner (e.g., by submitting an Incident Report Request with the Incident ID).

The Incident IDs provided by the AED may take a variety of form. In some circumstances it may be a unique identifier (UID) that cannot be utilized as an Incident ID by any other defibrillator or for any other incident. Such unique IDs can be constructed in variety of ways, as for example a concatenation of the AED's serial number (or a unique portion thereof) and the defibrillator's activation time. In some circumstance (particularly when the Incident ID is to be entered manually), it may be desirable to utilize shorter IDs that are more readily transcribed, even if the ID is not guaranteed to be unique. For example, a relatively short (e.g., 4-6 character long) alpha-numeric code can be used as the published Incident ID. The code can be created in any suitable manner, as for example, by a random or pseudo-random number generator, as a hash of selected information (e.g., the hash of a long unique ID associated with incident or the Incident Report itself), or in any other suitable manner. Although such a code may not be guaranteed to be unique, the odds can be quite high that there will be no overlap of codes in the timeframe relevant to retrieval of the defibrillator incident information. As such, even short and easily transcribable codes can work well for the intended purpose.

Furthermore, in some implementations, the AED network server may utilize other available information to help confirm/validate a match between a request and an available Incident Report. For example, the ePCR record will typically have a time of the incident and the location (e.g. geo-location) of the incident. Similarly, the defibrillator Incident Reports may record the time of the incident (e.g., the time that the AED was activated) and/or include the location of the incident (which may be available when the AED or an associated unit) has GNSS (e.g. GPS) services. Such time and/or location information, and/or other suitably available information can be compared for close proximity in reported times and/or reported locations of the incident to help verify that a particular Incident Report having the requested Incident ID is indeed the desired Incident Report. To facilitate such confirmation, Incident Report requests sent by the ePCR system to the AED network server may include both the time and location of the EMS incident in addition to the Incident ID. The AED network server, in turn, utilizes the time and location inputs to verify that an available Incident Report bearing the requested Incident ID match (i.e., are within reasonable ranges of) the time and location reported in the Incident Report.

FIG. 2 illustrated a workflow in which EMS personnel and ePCR systems serve as an intermediary for conveying defibrillator incident reports to the appropriate medical records systems. However, it should be appreciated that displaying or otherwise making the Incident ID available at the location of the incident and/or after the incident has occurred can be useful in a number of other workflows as well. For example, when the Incident ID is recorded in a patient's medical record, the attending doctor can request the incident record if it is not already present for any reason. Such requests can be facilitated with equally simple integrations between electronic medical records (eMR) system providers and the AED networks. The requests can be manually generated by attending medical personnel, or automatically initiated by a medical records system if/when an Incident ID is entered in a patient's record without the associated Incident Report. There are numerous circumstances where such integrations may be useful. One such example is when an AED user or a bystander is able to provide the Incident ID (e.g., a family member in the event of an in-home cardiac arrest incident or a trained volunteer responder). This can be particularly helpful in circumstances in which EMS are not called or doesn't use an integrated ePCR system, or doesn't enter the Incident ID into the ePCR system for any other reason. Another example use case is if/when the ePCR system was unable to retrieve a copy of the Incident Report prior to transferring the patient to a medical facility for any reason. Of course, there are a wide variety of other circumstances in which the medical provider may obtain the defibrillator Incident ID and wish to obtain the incident record or other information that the AED network may have about the incident.

To simplify integration with different ePCR systems, electronic medical record systems and other systems that may have reason to obtain defibrillator Incident Report, the AED network server may provide an API that standardizes the Incident Report requests. Such an API may include an Incident Report Request having at least the Incident ID, the incident location, and the incident time as parameters.

In other embodiments, the defibrillator incident reports can be delivered to the appropriate medical facilities using other approaches. For example, there are many communities (most often smaller and mid-sized cities and/or rural communities), there is a high probability or almost certainly that a cardiac arrest victim will be taken to a particular hospital/medical facility. If desired by the authorities responsible for overseeing EMS in such jurisdictions, the AED network server may be configured to proactively automatically send a received defibrillator Incident Report associated with an incident to the designated hospital any time a defibrillator creates an Incident Report for an incident that occurred within designated geographic boundaries. Again, this can be readily determined based on the incident location information provided in the Incident Report.

In some implementations, the Incident Report may be accessible on-line. That is, properly credentialed users may access the Incident Report on-line through a web-based interface or it can be downloaded from the website. As mentioned above, in some implementations, a barcode or the like, such as the QR code 310 illustrated in FIG. 3, may be displayed in addition to or in lieu of an alphanumeric identifier (e.g., Incident ID 315). The QR code may optionally include a URL that can be used to access the Incident Report. As will be appreciated by those familiar with QR code implementations, QR code readers can be configured to act upon URLs embedded in the QR code. For example, a QR codes/reader pair can be configured to automatically open a URL contained in the QR code when the QR code is scanned. Alternatively, the QR code/reader pair can be configured to prompt the user to open such a URL. Alternatively, when an app or application program receives a QR code with an embedded URL, the application can provide a GUI that facilitates accessing the Incident Report. Such applications may include defibrillator support applications executing on a mobile device such as a smart phone, a tablet computer, or other mobile communication device; an ePCR or other application executing on an EMS computer 30; etc.

The ability to access the Incident Report on-line can be useful in a variety of circumstances. For example, EMTs attending to the patient can access the Incident Report at any point after they have received the Incident ID. This can be at the scene of the incident, while transporting the patient to a hospital or at any other appropriate time. Medical personnel attending to the patient may access the Incident Report on-line in the same manner. If desired, the Incident Report may be made available on-line or via download to volunteer responder(s) and/or the AED's owner/administrator(s) and/or any other individual(s) as appropriate.

In some embodiments, a standardized "function" is used to create the QR code. For example, the inputs may include the serial number of the AED that created that incident log file and the activation time (when those items are used to create the Incident ID). The QR code (or other barcode) creates a URL link that is associated with the Incident ID—e.g., www.avive.life/incidentrepon/XXXXXXX (with "XXXs" representing the Incident ID. Since the QR code is created using a standardized function, it may be created by the AED itself, an interface unit associate with the AED, or an App executing on a mobile device (e.g. a Smartphone) that receives a status report or other communication that includes the Incident ID (or the elements used to create the Incident ID—e.g., the AED's serial number and the activation time).

Figure 4:
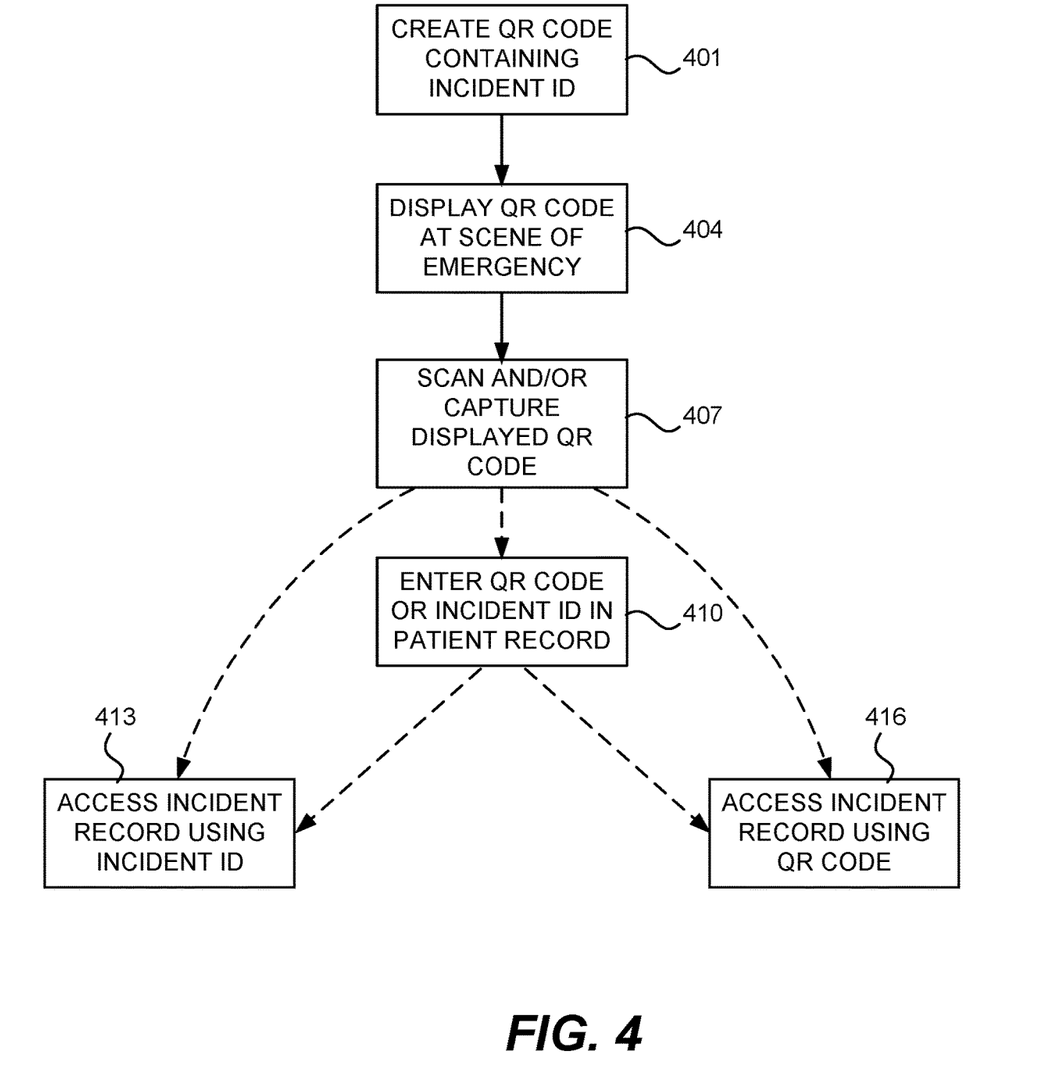
FIG. 4 is a flow chart illustrating methods of accessing incident records using barcodes that are created and scanned or captured at the scene of an emergency use of an AED.

The displaying of a barcode containing the Incident ID and optionally a URL at which the Incident Report can be obtained can be useful in a number of other workflows, some of which will be described with reference to FIG. 4. Initially, a QR code 300 is created that contains the Incident ID as represented by block 401. The QR code may optionally also include a URL of a website from which the Incident Report may be obtained or viewed. As discussed above, the QR code 300 may be created by the AED itself, or a device associated with the AED. For example, when a modular defibrillator system is provided that includes a base defibrillator unit and an interface unit as described in the incorporated U.S. Pat. No. 10,773,091, the QR code may be created by either the base defibrillator unit, or the interface unit. Alternatively, a smartphone (or other mobile communication device or other suitable external device), having a defibrillator support app installed thereon, may be configured to create the QR code. That is, an external device in proximity to the AED during or after the emergency use of the AED may receive the Incident ID from the AED. The associated defibrillator support app may then create the QR code based on the received Incident ID. In such embodiments, the Incident ID may be received via a wireless or wired connection with the AED, or via an advertisement broadcast by the AED (e.g., a BLE advertisement) and received by the mobile communication device functioning as a listener, as described in the incorporated U.S. patent application Ser. No. 16/733,591 (now U.S. Pat. No. 11,452,881).

Once the QR code has been created, it may be displayed as represented by block 404. Again, the QR code may be displayed on a display screen of the AED itself, an interface unit associated with the AED or a suitable external device as appropriate. The displayed QR code may then be scanned and/or captured by other devices as represented by block 407. An easy way to capture the QR code is to simply take a picture of the code.

Once the QR code has been scanned or otherwise captured, any of a number of things may be done using the code. For example, when the capturing device is an EMS computer 30 or a capture device associated with such a computer, the Incident ID and/or an image of the QR code itself may be entered into a patient record associated with the incident as represented by block 410.

Either the Incident ID or the QR code may be used to access the incident record as represented by blocks 413 and 416 respectively. Such access can be either on the spot, or at a later time. For example, the access may be by an ePCR system 40 as previously discussed, emergency services personnel, a doctor or other medical personnel involved with treating the patient, a medical records system, an administrator responsible for obtaining the incident record, emergency services personnel, the patient, a family member of the patient, or any other appropriately credentialed user having the Incident ID and/or QR code in hand. In some circumstances, the Incident Report may be provided in a downloadable and readily printable form such as a PDF. In others, the Incident Report may be made available on-line via web-access. It should be appreciated that the described approach provides a simple and intuitive mechanism for getting defibrillator incident information from an AED to medical personnel and others that can benefit from knowledge of the such information.

Although only a few embodiments of the invention have been described in detail, it should be appreciated that the invention may be implemented in many other forms without departing from the spirit or scope of the invention. For example, although specific examples have been given for getting an Incident ID into an ePCR record, it should be appreciated that other techniques can be used as appropriate. Similarly, although some specific Incident ID structures have been described, it should be apparent that a wide variety of different ID formats can be used as desired for a particular application.

As suggested above, in some embodiments an interface device associated with an AED may perform some of the functions attributable to the AED. The specific functions provided by the interface device may vary based on the respective capabilities of the AED and the interface device. For example, when the interface device has a display, the Incident ID (and any other desired information) may be displayed on the display of the interface device (which may be instead of or in addition to displaying the Incident ID on an AED screen). Similarly, the transmission of the Incident Report to the AED network server (or other appropriate recipient) may be accomplished via the interface device. In other implementations, such functionalities may be provided by a suitably configured mobile communication device.

In some embodiments, the incident log is compiled and encrypted by the AED after the AED is turned off following its use. Once the incident log has been completed, it is transmitted to the AED network server 20 using any available mechanism. In some embodiments, the AED transmits real-time status messages that include various information about the incident during emergency use of the AED. Such status messages may be forwarded or otherwise conveyed to the AED network server in real-time during the incident (i.e., during the emergency use of the AED), as described, for example in U.S. Pat. Nos. 10,773,091 and 10,737,105 and U.S. patent application Ser. Nos. 16/733,591 and 16/733,684 (now U.S. Pat. Nos. 11,452,881 and 11,077,312) each of which is incorporated herein by reference. The AED network server 20 can then use information received in such status messages, to provide real-time Incident Reports to medical personnel during emergency use of the AED. Although the information available from the real-time status messages transmitted during emergency use of the AED is expected to be less than the information available in the incident logs, the real-time Incident Reports can be beneficial in a variety of instances. For example, EMS personnel can call up the real-time Incident Reports to get some background on the incident prior to their arrival at the scene. Similarly medical personnel can get an understanding of the situation prior to the patient's arrival at a hospital (or other emergency medical facility). Of course, there are a variety of other uses of the real-time Incident Reports as well.

When available, both the incident log file and status messages forwarded to the AED Network Server may include the geo-coordinates of the incident (e.g., the GPS position). In the vast majority of situations, the time and location of the incident can be used to uniquely identify the defibrillator Incident Report associated with a particular incident even if/when the Incident ID is not available for any reason. This time/location approach can be useful for identifying the proper Incident Report in a wide variety of circumstances, as for example, when a responding EMT who has not yet arrived at the scene wants to access an Incident Report, when a doctor wishes to review the Incident Report before the patient has arrived, when no one recorded the Incident ID, etc. As should be apparent from the foregoing, the described embodiments should be considered illustrative and not restrictive and the invention is not to be limited to the details given herein, but may be modified within the scope and equivalents of the appended claims.

What is claimed is:

1. A method of communicating defibrillator incident information generated by a first automated external defibrillator (AED) to document a first emergency use of the first AED to treat a first victim during a first potential cardiac arrest incident, the first AED including a shock discharge capacitor and defibrillation electrode pads suitable for delivering a defibrillation shock to the first victim, and a display screen, the method comprising:

by the first AED, in association with the first emergency use of the first AED to treat the first victim, generating a first incident log that contains defibrillator event information related to the first emergency use of the first AED;

by the first AED, generating a first incident identifier that uniquely identifies the first emergency use of the first AED;

at a scene of the first incident, by the first AED, displaying the first incident identifier on the display screen of the first AED to facilitate entry of the first incident identifier into a first emergency services electronic patient care record associated with the first incident at the scene of the first incident;

electronically transmitting the first incident log directly or indirectly from the first AED to a remotely located management server, wherein the first incident log includes at least one of the first incident identifier, and elements that can be used to generate the first incident identifier;

at the management server, receiving a first electronic request from an Electronic Patient Care Record (ePCR) system for a first defibrillator report pertaining to the first emergency use of the AED, wherein the first request includes the first incident identifier that was entered into the first electronic patient care record associated with the first incident;

by the AED management server, generating a first incident report associated with the first incident, wherein the first incident report includes at least some incident information pertaining to the first incident from the first incident log; and by the management server, in response to the first request from the ePCR system that includes the first incident identifier, electronically transmitting the first incident report to the ePCR system for inclusion in the first electronic patient care record associated with the first incident;

and wherein the management server receives incident logs from a multiplicity of different AEDs, including the first AED and utilizes the first incident identifier received in the first request to uniquely determine that the first requested defibrillator report pertains to the first incident, whereby the management server transmits the first incident report to the ePCR system in response to the first request from the ePCR system that includes the first incident identifier.

2. A method as recited in claim 1 further comprising, by an emergency responder at the scene of the first potential cardiac arrest incident that occurs at a location that is not a medical facility, manually entering the first incident identifier into the first electronic patient care record associated with the first incident.

3. A method as recited in claim 1 wherein:
the first AED is a modular defibrillator system that includes a base defibrillator unit and an interface unit attached to the base defibrillator unit, wherein the base defibrillator unit is configured to function as an automated external defibrillator without the interface unit and the interface unit includes the display screen and a communications unit capable of electronically communicating with remotely located servers; and
the first incident log is transmitted from the interface unit to the management server; and
whereby the first incident identifier is displayed on the interface unit display screen.

4. A method as recited in claim 1 further comprising:
wirelessly transmitting the first incident identifier from the first AED to an ePCR input device at the scene of the first incident; and
at or by the ePCR input device automatically or semi-automatically entering the first incident identifier into the first electronic patient care record; and
wherein the first AED does not transmit the first incident log to the ePCR input device.

5. A method as recited in claim 1 wherein:
the management server is configured to receive incident logs from multiple different AEDs used in multiple different potential cardiac arrest incidents; and
the first defibrillator report request received from the ePCR system further includes at least one of a geo-location of the first incident and a time of the first incident.

6. A method as recited in claim 5 wherein the management server utilizes the at least one of the geo-location of the first incident and the time of the first incident in conjunction with the first incident identifier to help ensure, authenticate or verify that the correct incident report is transmitted to the ePCR system in response to the first report request.

7. A method as recited in claim 1 further comprising, by the first AED, generating and displaying on the display screen, a machine readable barcode that embeds the first incident identifier.

8. A method as recited in claim 7 further comprising, by an emergency responder, scanning the barcode to enter the first incident identifier into the ePCR system.

9. A method as recited in claim 7 wherein:
the barcode further embeds a representation of a URL of a website from which the incident report can be at least one of viewed or downloaded; and
the management server, receives the first electronic request via the website.

10. A method as recited in claim 7 wherein the barcode is a QR code.

11. A method as recited in claim 1 further comprising, an emergency responder transferring the first incident report to a medical facility record system together with the first electronic patient care record associated with the first incident.

12. A method as recited in claim 1 wherein the first incident report transmitted to the ePCR system is in the form of a PDF file.

13. A method of communicating defibrillator incident information created by a first automated external defibrillator (AED) to document a first emergency use of the first AED to treat a victim during a potential cardiac arrest incident, the first AED including a display screen, a shock discharge capacitor and defibrillation electrode pads suitable for delivering a defibrillation shock to the first victim, the method comprising:
by the first AED, in association with the first emergency use of the first AED to treat the victim, generating a first incident log that contains defibrillator event information related to the first emergency use of the AED;
by the first AED, generating a first incident identifier that uniquely identifies the emergency use of the AED;
by the first AED, generating a bar code that embeds the first incident identifier and a website URL;
by the first AED, displaying the bar code that embeds the first incident identifier and the website URL on the first AED's display screen;
electronically transmitting the first incident log directly or indirectly from the first AED to a remotely located AED management server, wherein the first incident log includes at least one of the first incident identifier, and elements that can be used to generate the first incident identifier and wherein the management server is configured to receive incident logs from a multiplicity of different AEDs, including the first AED;
by the AED management server, generating an incident report associated with the first incident, wherein the incident report includes at least some incident information pertaining to the first incident from the incident log;
by the management server, receiving a first request for a defibrillator report pertaining to the emergency use of the AED from a requester that, wherein the first request includes the first incident identifier and utilizes the URL; and
by the management server, in response to the first defibrillator report request, electronically transmitting the first incident report to the requester, wherein the management server utilizes the first incident identifier received in the first request to uniquely determine that the first requested defibrillator report pertains to the first incident, whereby the management server transmits the first incident report to the requester in response to the first defibrillator report request.

14. A method as recited in claim 13 wherein the first defibrillator report request is received from a medical records system, the method further comprising, receiving the first incident report at the medical records system and entering the first incident report in a patient record in the medical records system associated with the victim.

15. A method as recited in claim 13 wherein the first incident identifier is additionally output by the AED as part of a status message wirelessly broadcast by the first AED as an advertisement, using a wireless communications protocol, without requiring the establishment of a wireless connection between the first AED and a listener device that receives the status message.

16. A method as recited in claim 13 wherein the bar code is displayed at a scene of the incident and is recorded or captured in a manner that facilitates use of the recorded or captured first incident identifier in the first defibrillator report request.

17. A method as recited in claim 13 wherein:
the first AED is a modular defibrillator system that includes a base defibrillator unit and an interface unit attached to the base defibrillator unit, wherein the base defibrillator unit is configured to function as an automated external defibrillator without the interface unit and the interface unit includes the display screen and a communications unit capable of electronically communicating with remotely located servers; and
the first incident log is transmitted from the interface unit to the management server; and
whereby the bar code is displayed on the interface unit display screen.

18. A method as recited in claim 17 wherein the first incident identifier is additionally output by the first AED as part of a status message wirelessly broadcast by the base defibrillator unit as an advertisement, using a wireless communications protocol, without requiring the establishment of a wireless connection between the base defibrillator unit and a listener device that receives the status message.

19. A method as recited in claim 13 further comprising displaying an alphanumeric representation of the first incident identifier in parallel with displaying the bar code.

20. A method of communicating defibrillator incident information created by an automated external defibrillator (AED) to document an emergency use of the AED to treat a victim during a potential cardiac arrest incident, the AED being a modular defibrillator system that includes a base defibrillator unit and an interface unit attached to the base defibrillator unit, wherein the base defibrillator unit includes a shock discharge capacitor and defibrillation electrode pads suitable for delivering a defibrillation shock to the victim, and is configured to independently function as an automated external defibrillator without the interface unit and the interface unit includes a display screen and a communications unit capable of electronically communicating with remotely located servers, the method comprising:
by the AED, in association with an emergency use of the AED to treat the victim, generating an incident log that contains defibrillator event information related to the emergency use of the AED;
by the AED, generating an incident identifier that uniquely identifies the potential cardiac arrest incident;
by the interface unit, generating a bar code that embeds the incident identifier and a URL of a website;
by the AED, displaying the bar code that embeds the incident identifier and the URL on the display screen together with an alphanumeric representation of the incident identifier;
by the AED, generating a status message that includes the incident identifier;
by the AED, wirelessly broadcasting the status message as an advertisement using a wireless communications protocol, without requiring the establishment of a wireless connection between the AED and a listener device that receives the status message;
electronically transmitting the incident log directly or indirectly from the interface unit of the AED to a remotely located AED management server, wherein the incident log includes at least one of the incident identifier, and elements that can be used to generate the incident identifier;
by the AED management server, generating an incident report associated with the incident, wherein the incident report includes at least some incident information pertaining to the incident from the incident log;
by the management server, receiving a request for a defibrillator report pertaining to the emergency use of the AED from a requester, wherein the request includes the incident identifier, and is directed to the management server using the URL; and
in response to the defibrillator report request, electronically transmitting the incident report to the requester.

* * * * *